United States Patent
Feucht (10) Patent No.: US 6,737,618 B2
(45) Date of Patent: May 18, 2004

(54) MAGNETIC COIL APPARATUS FOR HEATING MAGNETIC SUBSTANCES IN BIOLOGICAL TISSUE

(75) Inventor: Peter Feucht, Berlin (DE)

(73) Assignee: MFH Hyperthermiesysteme GmbH, Berlin (DE)

( * ) Notice: Subject to any disclaimer, the term of this patent is extended or adjusted under 35 U.S.C. 154(b) by 169 days.

(21) Appl. No.: 10/081,414

(22) Filed: Feb. 22, 2002

(65) Prior Publication Data

US 2002/0125975 A1 Sep. 12, 2002

(30) Foreign Application Priority Data

Feb. 24, 2001 (DE) ........................... 101 09 105

(51) Int. Cl.[7] ............................... H05B 6/10
(52) U.S. Cl. ........................ 219/635; 219/670
(58) Field of Search ............ 219/635, 670, 219/632, 647, 672, 677; 336/60; 324/319; 600/9, 13, 10, 14, 15; 607/103, 115, 154

(56) References Cited

U.S. PATENT DOCUMENTS 5,415,617 A * 5/1995 Kraus ..................... 600/13
5,935,476 A * 8/1999 Langstedt ................ 219/659
6,445,185 B1 * 9/2002 Damadian et al. .......... 324/319

* cited by examiner

Primary Examiner—Quang T. Van
(74) Attorney, Agent, or Firm—McNair Law Firm, PA; Cort Flint (57) ABSTRACT

A magnetic coil arrangement for a magnetic field applicator (1) which heats magnetic or magnetizable substances or solids in biological tissue is disclosed which includes a coolable magnetic yoke (2) with two spaced, opposing pole shoes (7, 8) separated from each other by a exposure volume gap (12) on the magnetic yoke (2). A magnetic coil (22) is assigned to each of the two pole shoes (7, 8) to produce a magnetic alternating field. The magnetic coils are designed as disk coils with helicoidally extending coil windings (39) respectively surrounding the pole shoe end of the assigned pole shoe (7, 8) with a surrounding magnetic coil/pole shoe gap (57). According to the invention, the magnetic coil (22) is respectively arranged in a coil box annularly surrounding the assigned pole shoe (7, 8), with the coil box (9, 10) being provided with at least one cooling air admission port (51, 52, 53) for connection of a cooling air pump and with at least one cooling air discharge port (57, 66).

21 Claims, 5 Drawing Sheets

MAGNETIC COIL APPARATUS FOR HEATING MAGNETIC SUBSTANCES IN BIOLOGICAL TISSUE

BACKGROUND OF THE INVENTION

The invention relates to a magnetic coil arrangement of a magnetic field applicator for treating biological tissue, and more particularly a magnetic oil arrangement for heating magnetic or magnetizable substances or solids in biological tissue.

Cancer diseases can be treated in a generally known manner by means of hyperthermia processes, wherein cancer tissue is specifically heated to temperatures of approximately 41° C. to 46° C. for irreversible damage. In a known hyperthermia process (WO 97/43005) for tumor therapy, magnetizable microcapsules are used which reach the area of the tumor through the blood stream. During a treatment, these microcapsules are charged with a magnetic alternating field generated outside of a patient, with hysteresis effects generating heat for hyperthermia in the microcapsules. A linear magnetic alternating field is used with a frequency in the range of 10 kHz to 500 kHz. The microcapsules should contain a highly magnetizable material so that the force of the magnetic alternating field, the required instrumentation structure, the required cooling system as well as the electrical energy supply can be manageable. A practical instrumentation structure is however not indicated.

In a very much similar, known hyperthermia process (EP 0 913 167 A2), rotating magnetic fields with a frequency in the range greater than 10 kHz are used as fields. To produce the rotating magnetic alternating fields a magnetic field applicator is indicated only sketchily and schematically.

A generic magnetic coil arrangement is shown in the (post-published) DE 199 37 492 publication. The magnetic field applicator for heating magnetic or magnetizable substances in biological tissue comprises a coolable magnetic yoke with two pole shoes facing each other and being separated by a gap to define an exposure volume on the magnetic yoke. To produce a magnetic alternating field, two magnetic coils are assigned to one pole shoe each. The magnetic coils are designed as disk coils with helicoidally extending coil windings and annularly surrounding the pole shoe end of the assigned pole shoes with an intermediate, circulating magnetic coil/pole shoe gap. The magnetic yoke and the pole shoes consist of ferrite block segments which are mounted together.

For hyperthermia, in particular with magnetic liquids, alternating field forces of approximately 15 to 20 kA/m at approximately 50 to 100 kHz are required. With a volume exposed by a magnetic field of 8 to 30 I, effective power of approximatelyl 18 kW to 80 kW must be produced by a hyperthermia installation. This energy must be produced in form of high frequency and must then be transmitted in form of heat with cooling since only a few watts are produced in the magnetic fluid for the hyperthermia in a patient's body. For cooling of the ferrite block segments, the magnetic yoke and the pole shoes, measures are specified with cooling air flow in cooling gaps. In contrast, the type of cooling of the magnetic coils as well as their mounting system is left open. However, cooling of the magnetic coils is problematic since there is a particularly high power loss which is higher per volume unit than the power loss in the ferrite block segments and since only a relatively small specified space for installation in the magnetic coil area is available for cooling devices and mounting systems.

It is therefore the object of the present invention to develop an improved magnetic coil arrangement for a magnetic field applicator to heat magnetic and magnetizable substances or solids in biological tissue so that effective cooling of the magnetic coils will be possible in combination with a compact arrangement and mounting.

SUMMARY OF THE INVENTION

The above objective is accomplished according to the present invention by providing a magnetic coil in a coil box annularly surrounding the assigned pole shoe. The coil box comprises at least one cooling air admission port for connection to a cooling air pump and at least one cooling air discharge port. Magnetic yoke cooling and magnetic coil cooling can be advantageously isolated and optimally adjusted to the different cooling requirements in terms of cooling air volume, cooling air pressure, and cooling air throughput and cooling air flow. Moreover, the coil box can be used, in addition to its duty as part of the magnetic coil/cooling device, for mechanically mounting the magnetic coil. Thus, an advantageously compact design is provided which is well suited to the confined space conditions of a magnetic field applicator in the area of the gap of the exposure volume and a patient's body areas. In a preferred embodiment, the magnetic yoke and the pole shoes consist of assembled ferrite block segments. The magnetic yoke is combined of cut-stone-shaped ferrite block segments, the surfaces of which are freed from sintering layers and, if necessary, ground to be plane-parallel. The cut-stone-shaped ferrite block segments consist of ferrite plates lined up in a row, aligned in the magnetic yoke along the magnetic flow. The ferrite plates are separated from each other by an insulation/cooling gap transverse to the magnetic flow through which cooling air for magnetic yoke cooling is conveyed. In the direction of magnetic flow, adjacent ferrite plates are separated only by narrow contact gaps. To form the insulation/cooling gap, plastic separators are inserted between the ferrite plates. The cut-stone-shaped ferrite block segments are formed by bonding together the ferrite plates and the separators. The pole shoes are cylindrically or round, as seen from the top, and have a similar structure of wedge-shaped ferrite block segments which are assembled like pieces of a pie. Between these ferrite block segments, insulation/ cooling gaps are also provided by means of separators for pole shoe cooling.

The power losses caused in the ferrite block segments during operation of a magnetic field applicator are so high that they are dissipated by introduction of cooling air into suitably designed insulation/cooling gaps between the ferrite block segments. It has been shown, however, that a possible combination of the magnetic coil cooling and the magnetic yoke and pole shoe cooling is difficult to design, expensive and ineffective. One problem with the possible combination is the fact that the magnetic coil produces a higher power loss in comparison per volume unit. Thus, especially with the arrangement and isolation of the cooling systems according to the present invention provide considerable benefits regarding the arrangement, dimensioning and operation of the two cooling systems. Moreover, its simple assembly also reduces the expenditures for installation, handling and maintenance as well as operating costs.

According to one aspect of the invention, the pole shoe end surfaces are each covered by a pole shoe plate. A laterally surrounding pole shoe plate extends beyond the assigned pole shoe end surface and forms a coil box bottom wall on the side of the exposure volume. Separators are inserted between the pole shoe end surfaces and the pole shoe plate to create insulation/cooling gaps. These separators are relatively small compared with the contact surface of the wedge-shaped ferrite block segments so that a cooling air flow through the separators passes radially between pole shoe end surface and pole shoe plate will hardly be obstructed. The pole shoe plate, in the area of the pole shoe end surface, has an indentation which is less thick than an adjacent area of the coil box bottom wall. The pole shoe end surface extends some-what into this indentation with the surrounding edge of the pole shoe end surface being rounded off. A surrounding annular gap is created as a cooling air outlet between the pole shoe plate and the pole shoe end surface. In this annular gap, it is possible to bypass the radial cooling air flow to an axial outlet direction. The pole shoe plate may be made of insulating material, such as glass. However, a high-quality, fiberglass reinforced plastic is preferably used, and the afore-mentioned indentation can be made by routing.

In an embodiment which is simple to make and functional in design the pole shoes are circular as seen from the top and the magnetic coils are accordingly designed in form of a circular ring. However, the associated coil boxes should be designed cut-stone-shaped with regard to their outer dimensions and surround the pole shoe ends as well as the magnetic coils placed above. On the one hand, a cut-stone-shaped design of the coil boxes results in simple manufacture since no bent wall parts must be connected with each other. Moreover, a favorable arrangement of cooling air admission ports will result which may be arranged either on the coil box side walls and/or in preferably two opposite corner areas of the coil box top wall. With these technically advantageous air admission designs, the required ports as well as flange connections for cooling hoses to be connected can be made with little expenditure.

In another preferable development, the magnetic coil is provided with a support structure for the windings. In the area of the magnetic coil, web-shaped bottom side coil carriers below web-shaped top side coil carriers are provided as coil carrier pairs which are assigned to each other and which are radially arranged in form of rays and angularly spaced to each other like spokes. The assigned coil carrier pairs are each connected by insulating rods which are radially at a distance. The coil carrier pairs are approximately, axially aligned so that retention sections are formed between the insulating rods in which the helicoidally extending coil windings are taken up and held. Due to the web height of the bottom side coil carriers, the coil windings are raised versus the coil box bottom wall forming a radially exterior annular cooling air inlet gap. Cooling air can then be further axially conveyed through this annular cooling air inlet gap and through the intermediate gap defined by the insulating rods between the coil windings. A top cutout section, preferably a circular top gap between the top side coil carriers, which are not covered above the coil windings, will be used as the cooling air discharge port. The height and length of the coil carriers as well as the insulating rods are to be selected such that, on the one hand, the windings will be sufficiently supported and held and, on the other hand, that the insulation distances between the windings comply with the regulations on air and creepage distances, and that sufficient cooling air can be conveyed between them. Particularly advantageous conditions result according to the invention if the insulating rods are designed as round ceramic rods. A practical support structure tested with good results consists of 16 coil carrier pairs with six insulating rods each with five winding retention sections each resulting thereby. The coil windings are designed of a strand of very fine RF wires. The coil box and the support structure for the magnetic coil can each be manufactured alike for the top and the bottom pole shoe. Since, however, the pole shoe plate in the arrangement on the bottom pole shoe faces toward the top, the top-side coil carriers bear the weight of the assigned magnetic coil.

In an advantageously designed further development according to the invention, the coil box bottom wall, the coil box side walls, the coil box top wall as well as a thin-walled wind box inside wall will form a surrounding wind box with a bottom side annular cooling air inlet gap. Moreover, the magnetic coil is surrounded radially on the inside by an air guide wall so that an annular gap is created for the discharge of the pole shoe cooling air between the air guide wall and an adjacent pole shoe wall. In this case, the pole shoe cooling air and the magnetic coil cooling air are separate from each other in the area of this air guide wall and advantageously isolated. The wind box, as a pressure chamber, can be charged with cooling air which is then preferably conveyed via the bottom side annular cooling air inlet gap to the bottom coil winding areas where maximum heating of the magnetic coil takes place, and subsequently is dissipated between the coil windings. Another important improvement of the magnetic coil cooling results from the coil carriers being designed wedge-shaped so that the radially exterior coil windings, with their bottom side coil winding areas, are raised more from the coil box bottom wall than the coil winding areas which are lying radially further inside. Thus, cooling air will be conveyed through the bottom side annular cooling air inlet gap and impinged on the spaced lower edges of the coil windings, where maximum heating of the coil takes place through eddy currents in the copper due to the generated magnetic field. Due to the wedge-shaped design especially of the bottom side coil carriers and the resulting cross-sectional constriction toward the center, the advantageously high air velocity results on the innermost coil winding, i.e. where there is the maximum need for cooling. Cooling air here flows through the winding spacings and can freely leave above the magnetic coil with no further bottlenecks arising. To further convey the cooling air flow to the radially inner coil winding area, at least one approximately bottom-parallel air baffle plate can be arranged starting from the annular cooling air inlet gap. Advantageously, two air baffle plates, one atop the other, are each provided in the area between two bottom side coil carriers, with the air baffle plate which is closer to the bottom to be designed longer and wider. These air baffle plates can simply be screwed to the coil box bottom wall by means of spacers and/or distance rings.

The coil carriers may be provided with location holes for holding the insulating rods, and the bottom side coil carriers may be screwed and/or bonded with the coil box bottom wall, in particular the pole shoe plate. In contrast, the topside coil carriers are radially screwed to the top wall and are detachable on the outside. On the inside, the coil carriers are detachably screwed via support columns with the coil box bottom wall. The detachability of the topside coil carriers is essential for simple assembly of the coil windings. A solid coil box is created through screw and/or bonding connections between the coil box bottom wall, the coil box side walls and the coil box top wall. The coil box is connectable via additional connecting elements such as for example threaded rods with adjacent magnetic yoke elements. A pole shoe plate is stiffened through its lateral connection with the coil box side walls so that it has advantageously only a slight sag although, if necessary, a routed indentation may be provided in the pole shoe area.

An especially preferable combination of the arrangement in accordance with the invention results from a magnetic yoke form known per se according to claim 13 in the type of an M-shape as a three-legged arrangement.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Referring now in more detail to the drawings, the invention will now be described in more detail. As can best be seen in FIG. 1, a magnetic field applicator 1 for hyperthermia is schematically illustrated for heating a magnetic or magnetizable substance or solids in affected body tissue. A tumor zone in a human body into which a liquid with e.g. magnetic nano-particles are incorporated is especially well suited as body tissue to be provided with fields, whereby the tumor zone can be heated to temperature values preferably above approximately 41° C. The magnetic field applicator 1 comprises a magnetic yoke 2 designed in a general M shape having a three leg arrangement which includes two parallel vertical yoke elements 3, 4 spaced from each other and two transverse yoke elements 5, 6 connected between them.

There is a lower transverse yoke element 6, and an associated lower pole shoe 8 surrounded by a lower coil box 10. There is an upper transverse yoke element 5 and an associated upper pole shoe 7 surrounded by upper coil box 9. The coil boxes are disposed within a portal defined by two vertical yoke elements 3, 4. The yoke elements can be displaced by means of a self-inhibiting spindle drive 11 shown schematically, in order to adjust the width of the gap defining exposure volume 12. It can furthermore be seen in FIG. 1 that an exposure volume gap 12 is delimited by bulkheads 14, 15 which define an intersection space 13. The bulkheads 14, 15 can be adjusted vertically relative to each other.

Figure 2:
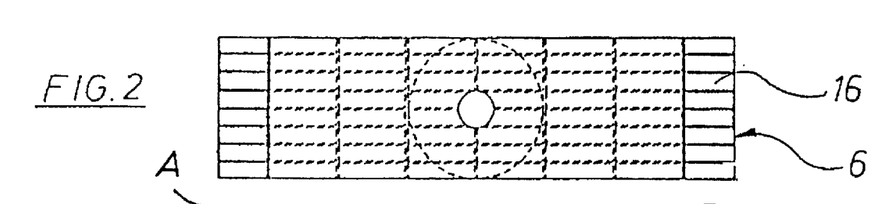
FIG. 2 is a schematic top view on the magnetic field applicator of FIG. 1.
Figure 3:
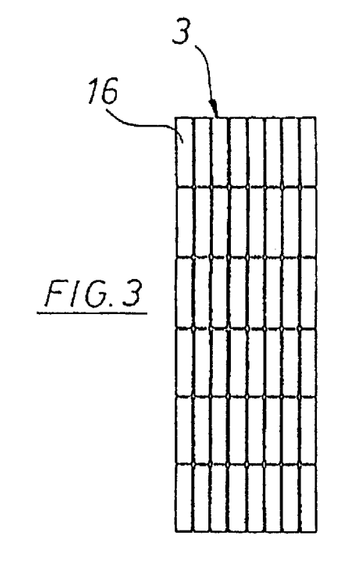
FIG. 3 is a schematic side view of the magnetic field applicator of FIG. 1.
Figure 4:
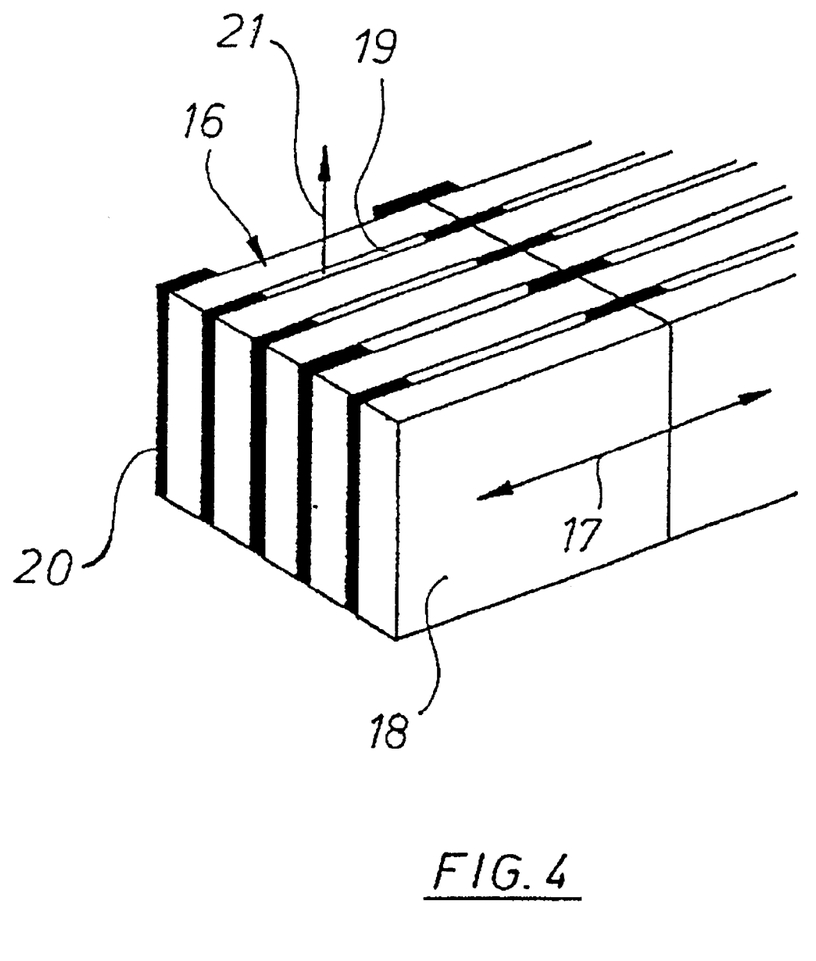
FIG. 4 schematically shows a perspective and enlarged representation of the structure of the hew-stone-shaped ferrite block segment constructed according to the present invention.

As can be seen in FIGS. 2 and 3, respectively showing a side top view and a side view of magnetic yoke 2. Magnetic yoke 2 is composed of cut-stone-shaped ferrite block segments 16. The surfaces of the blocks are free of sintering layers and are ground plane-parallel. Ferrite block segments 16 include ferrite plates 18 aligned in rows in magnetic yoke 2 in a direction of magnetic flow 17. Ferrite plates 18 are separated from each other transverse to the direction of magnetic flow 17 by insulation/cooling gaps 19 (FIG. 4). Plastic separators 20 are inserted between the plates in insulation/cooling gap 19. Ferrite plates 18 and plastic separators 20 are bonded to form ferrite block segments 16 which form the yoke elements. Cooling air can be conveyed through the insulation/cooling gaps 19 to cool magnetic yoke 2 as shown schematically in FIG. 4 by arrow 21.

Figure 1:
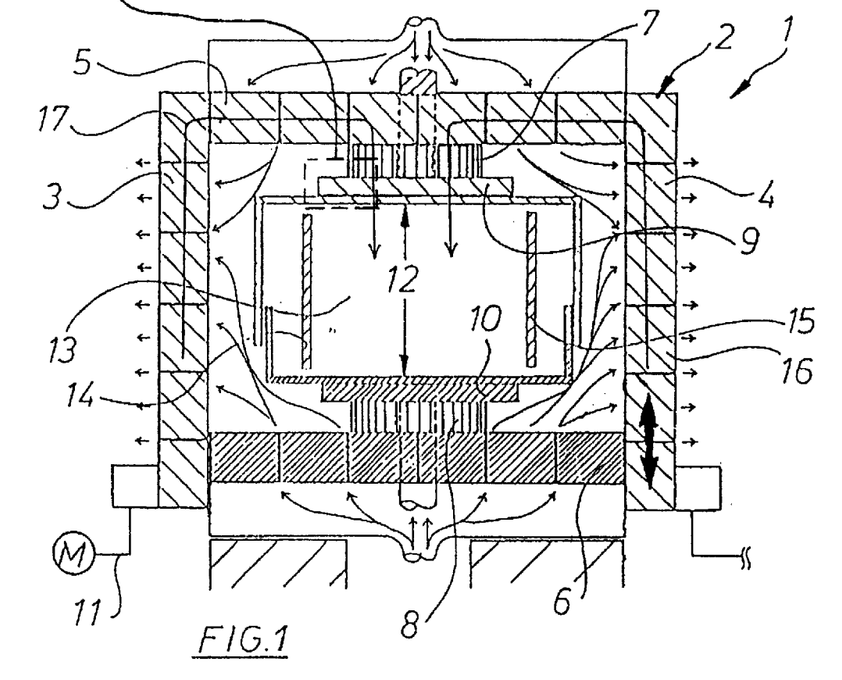
FIG. 1 is a schematic sectional view taken through a magnetic field applicator constructed according to the present invention.
Figure 5:
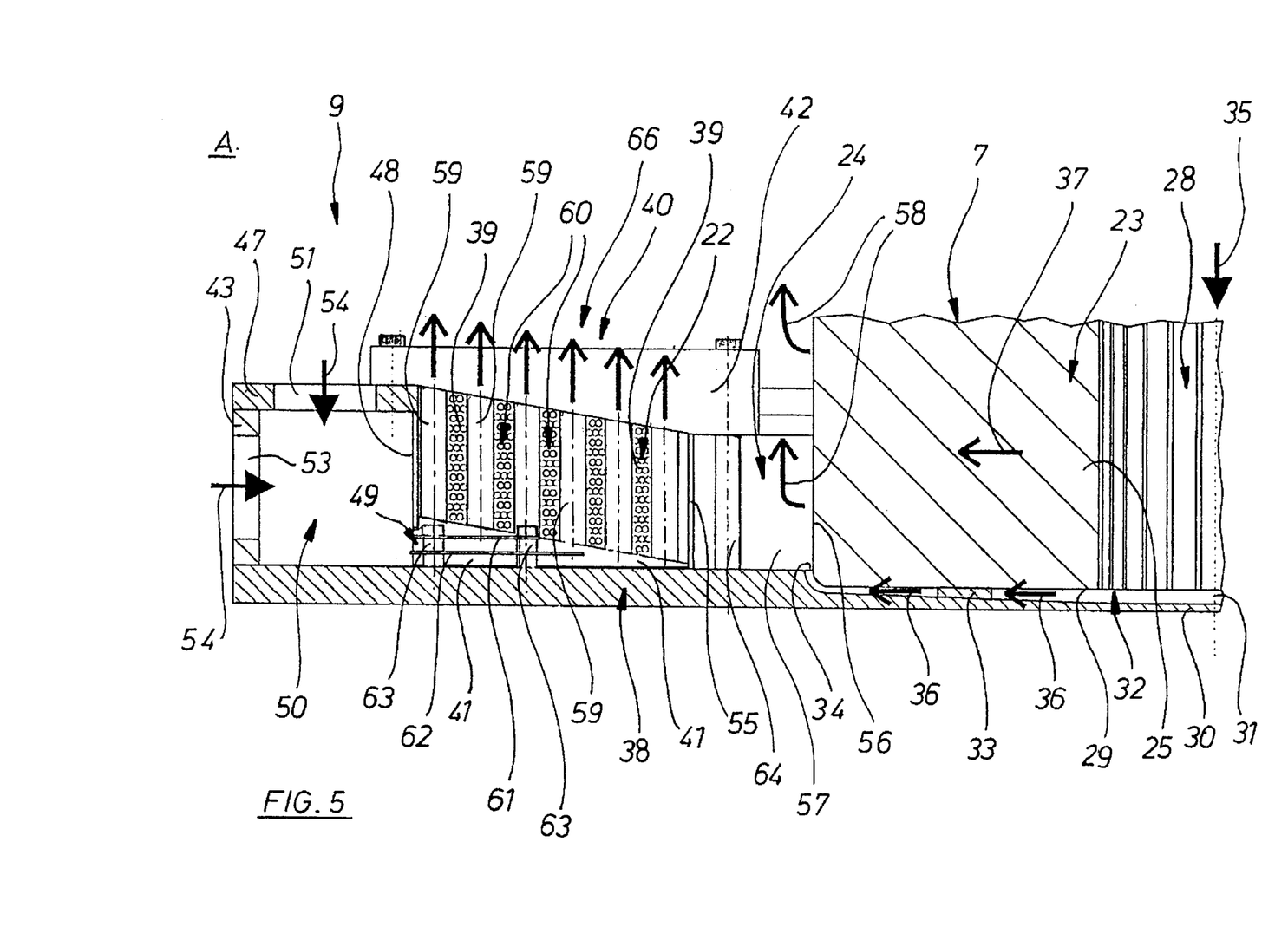
FIG. 5 is a schematic enlarged representation of detail A of FIG. 1

As is shown in particular in FIG. 5, which is an enlarged detailed view of detail A of FIG. 1, pole shoe 7 is assigned a magnetic coil 22 for the generation of a magnetic alternating field. Coil 22 is designed as a disk coil with helicoidally extending coil windings 39 and circularly surrounding a pole shoe end of pole shoe 7. A surrounding magnetic coil/pole shoe gap 24 is created between the magnetic coil and the pole shoe end. The structure of bottom pole shoe 8 and bottom coil box 10 is identical in design to that described in connection with top pole shoe 7 and top coil box 9, as well as in connection with magnetic coil 22.

Figure 6:
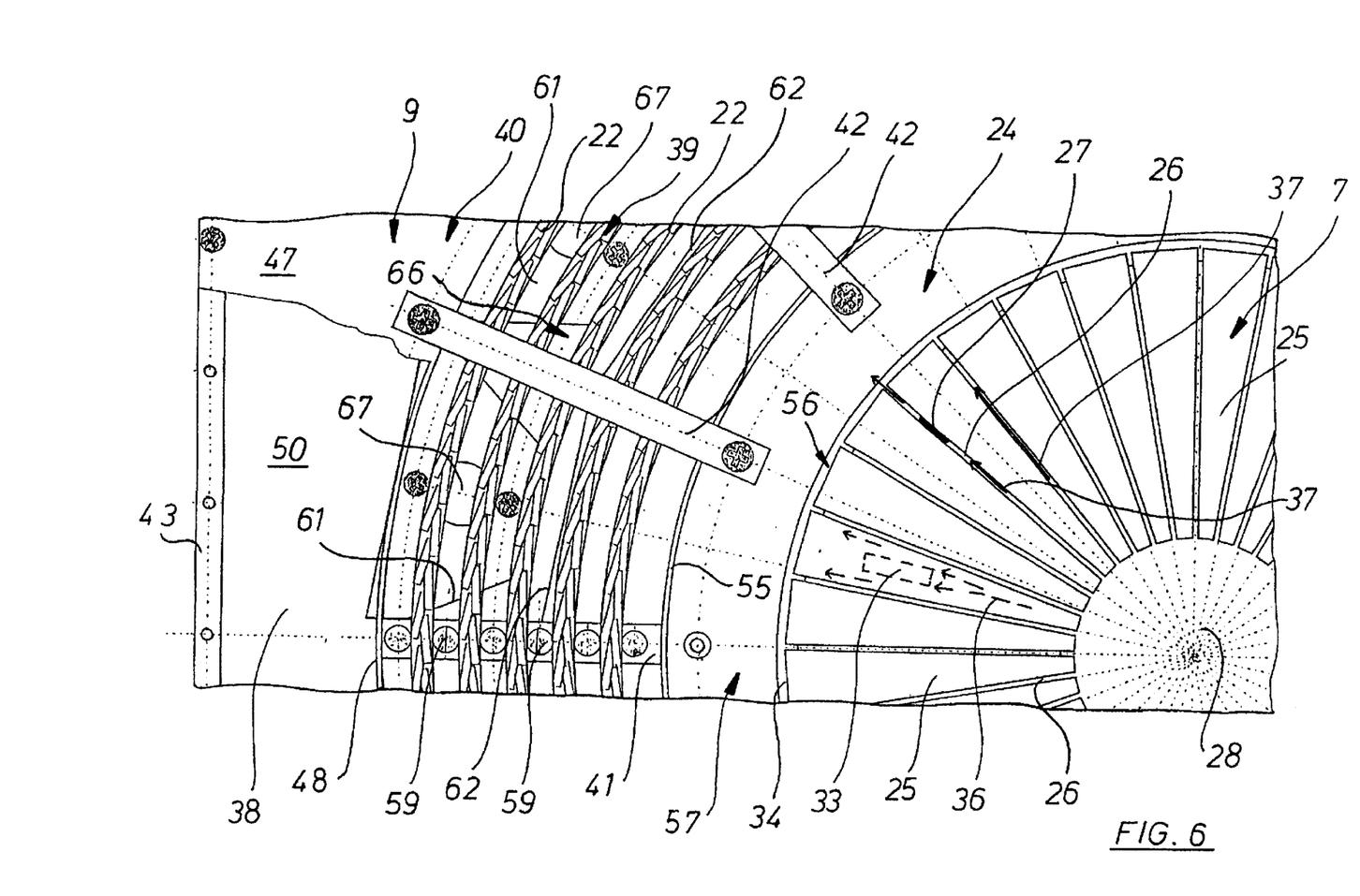
FIG. 6 is a schematic, enlarged top view according to FIG. 5.
Figure 8:
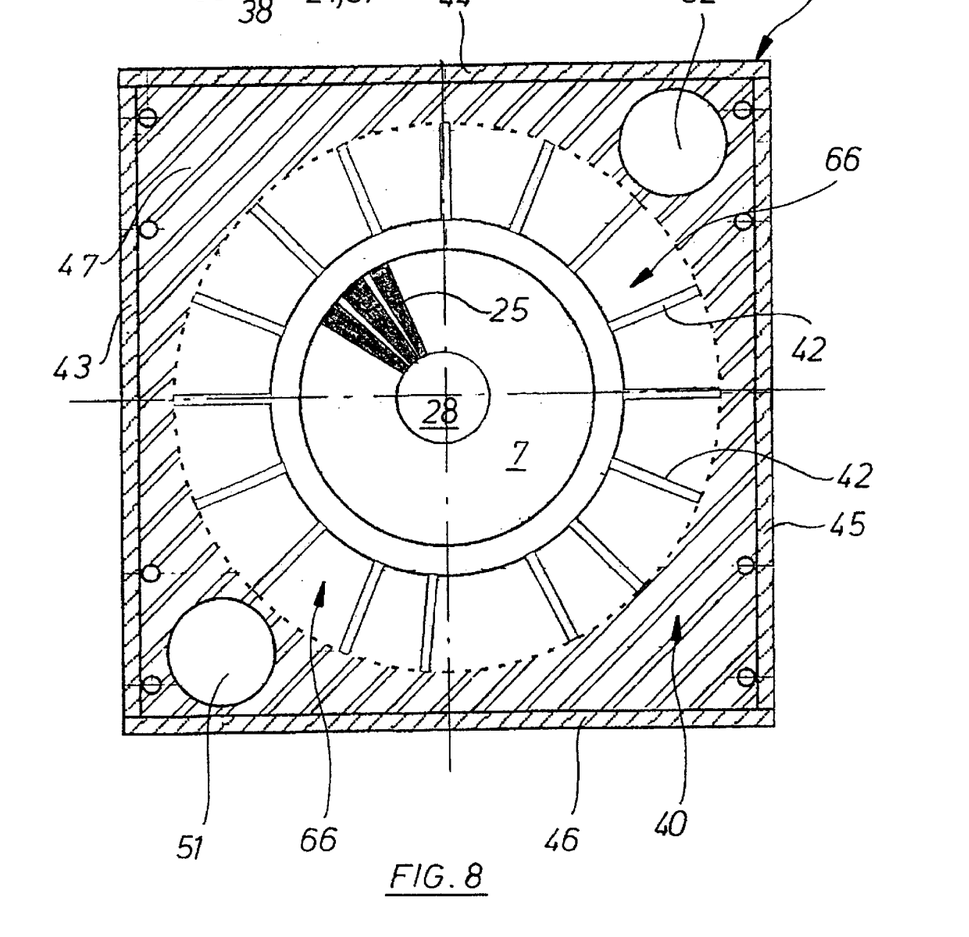
FIG. 8 is a schematic top view on a coil box with assigned pole shoe and assigned magnetic coil constructed according to the present invention.

Pole shoes 7, 8 are circular in cross-section, and assembled from correspondingly machined ferrite block segments which are wedge shaped as seen from the top, as can best be seen in FIG. 6 which is an enlarged top view of FIG. 5, and from FIG. 8 which shows a top view of top coil box 9 and top pole shoe 7.

Insulation/cooling gaps 26 are formed between the wedge-shaped ferrite block segments 25 by separators 27 respectively inserted, only one of which is schematically and exemplarily shown in FIG. 6. Adjacent ferrite block segments 25 are bonded together by separators 27 to form pole shoe 7. Pole shoe 7 furthermore comprises an axial tubular opening 28 to form a tubular pole shoe 7.

As can be seen in FIG. 5, the pole shoe end surface 29 of pole shoe 7 is covered by a pole shoe plate 30. Pole shoe plate 30 laterally extends beyond the pole shoe end surface 29 and has an indentation 31 in a pole shoe and area of the pole shoe end surfaces 29 which is less thick than the remaining area of the pole shoe plate 30 surrounding the pole shoe end. Between pole shoe end surface 29 and pole shoe plate 30, separators 33 are inserted to form insulation/cooling gaps 32 (only one is shown schematically and exemplarily in FIGS. 5 and 6). The surrounding edge of the pole shoe end surface 29 is rounded off, like the assigned edge of indentation 31 so that the insulation/cooling gap 32 ends in an annular gap 34 as a cooling air outlet. As shown in FIG. 5 cooling air according to arrow 35 can be conducted to pole shoe 7 via opening 28. This cooling air then flows between the individual ferrite block segments 25 through the indentation-side insulation/cooling gap 32 and the annular gap 34 according to arrows 36, and via the insulation/cooling gap 26 according to arrows 37, as shown in FIGS. 5 and 6.

As can best be seen in FIG. 5 in combination with FIG. 8, top coil box 9 is designed in cut-stone shape, with the laterally surrounding and protruding area of the pole shoe plate 30 of the assigned pole shoe end surface 29 forming a coil box bottom wall 38 on the side of the gap exposure volume. As shown in FIG. 8, coil box side walls 43, 44, 45, 46 connect to the coil box bottom wall 38. A coil box top wall 47 is placed on top of coil box side walls 43, 44, 45, 46 (FIGS. 5 and 8). Moreover, coil box 9 comprises a thin-walled wind box inside wall 48, surrounding magnetic coil 22 radially and spaced from coil box bottom wall 38 to define an annular cooling air inlet gap 49. Coil box bottom wall 38, coil box side walls 43, 44, 45 and 46, the coil box top wall 47 as well as the wind box inside wall 48 form a surrounding wind box 50. The cooling air supply to wind box 50 is supplied via top wall side admission ports 51, 52 and admission ports 53 in the side walls. A cooling air pump, here not shown, can be connected to these cooling air admission ports 51, 52, 53 to supply cooling air according to arrows 54 can be blown into wind box 50. Magnetic coil 22 is surrounded by an air guide wall 55 radially on the inside whereby an annular gap 57 is formed between adjacent pole shoe wall 56, for discharge of the pole shoe cooling air according to arrows 58.

There is a support structure 40 for coil windings 39 of magnetic coil 22 which includes web-shaped bottom side coil carriers 41 and web-shaped top side coil carriers 42, above coil carriers 41, as assigned coil carrier pairs. As shown in FIG. 6 and FIG. 8, the assigned coil carrier pairs of bottom side coil carriers 41 and top-side coil carriers 42 are each arranged radially in form of rays and angularly spaced from adjacent coil carrier pairs. In FIG. 6, one of the one of the coil carrier pairs is presented without top-side coil carrier 42. FIG. 5 shows that coil carriers 41, 42 assigned to each other in pairs are connected by insulating rods 59 which are spaced radially and approximately axially aligned. Insulating rods 59 are designed, for example, as round ceramic rods, with retention sections 60 being formed between insulating rods 59 in which the helicoidally extending coil windings 39 are disposed. As shown in FIG. 5, coil carriers 41, 42 are each wedge-shaped in design so that the radially exterior coil windings, with their bottom-side coil winding areas, are more raised from the coil box bottom wall 38 than the coil winding areas which are radially further on the inside.

Starting from annular cooling air inlet gap 49 in the wedge area between coil carriers 41 on the bottom side, air baffle plates 61, 62 extend approximately parallel with the bottom. The air baffle plate 62 which is closer to the coil box wall bottom is longer and wider in design than above arranged air baffle plate 61. The air baffle plates 61, 62 are connected via columns 63 with coil box bottom wall 38.

Figure 7:
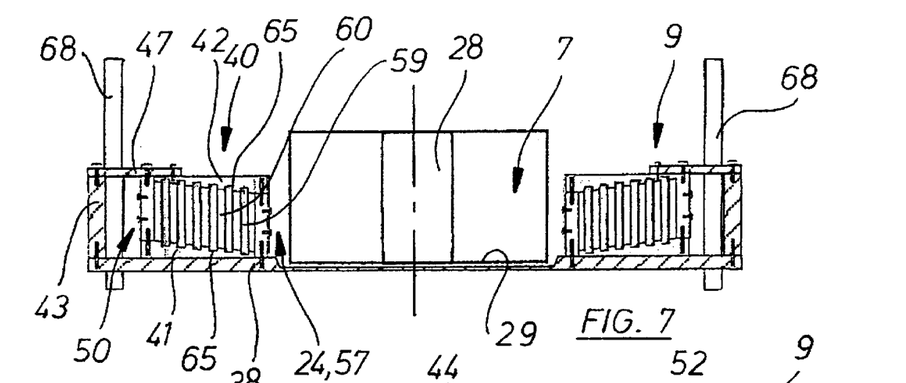
FIG. 7 is a schematic cross-section through a top coil box together with the assigned pole shoe according to an alternate embodiment.

As can be seen in FIG. 5 and FIG. 6, the top-side coil carriers 42 are detachably fastened, such as by screws to top wall 47, and on the inside detachably screwed to support columns 64 provided on coil box bottom wall 38. In FIG. 7, which shows a schematic cross section through the coil box 9, an alternate embodiment is shown in which the top-side coil carriers are screwed from the bottom to top wall 47. Moreover, threaded rods 68 are also arranged on the edge through which a connection is possible with other components. Otherwise, the structure corresponds with that shown in the enlarged detailed presentation of FIG. 5. Coil carriers 41 on the bottom side are screwed and/or bonded with the coil box bottom wall 38. As shown in FIG. 7, coil carriers 41, 42 can each have location holes 65 in which the insulating rods 59 are inserted and held.

Referring to FIG. 5, cooling air is conveyed via the wind box 50 which functions e.g. as a pressure chamber, via the annular cooling air inlet gap 49 on the bottom side of the lower coil windings areas which is the place of maximum heating of magnetic coil 22. Due to the radially exterior coil windings with their coil winding areas on the bottom side being raised further from the coil box bottom wall 38 than the coil winding areas which are radially on the inside, the cooling air conveyed via the annular cooling air inlet gap 49 impinges directly on the staggered bottom edges of the coil windings 39, where the maximum heating of the coil takes place through eddy currents in the copper due to the generated magnetic field. Due to the wedge-shaped design and the cross-section constriction toward the center, the advantageously maximum air velocity will occur in this bottom area on the innermost coil winding, i.e. where the cooling need is the highest. Here, cooling air flows through the windings and can freely leave above the magnetic coil 22 in the gap area 66 of the coil windings which are not covered (FIG. 8). Gap areas 66 form cooling air discharge ports. Especially through air baffle areas 61, 62, the cooling air flow to the coil winding area is promoted radially on the inside since partial air flows are branched off directly starting from the annular cooling air inlet gap which can only flow toward the top of this coil winding area radially on the inside. A flow-through port 67 toward the top can be designed in air baffle plate 61. This will provide more air to the outer windings in connection with the air baffle plates 61, 62 (FIG. 6).

What is claimed is:

1. A magnetic field applicator having a magnetic coil arrangement for heating magnetic or magnetizable substances or solids in biological tissue, of the type having a coolable magnetic yoke with first and second pole shoes facing each other separated by a exposure volume gap the magnetic yoke, two magnetic coils for the production of a magnetic alternating field, each of which is assigned to a pole shoe, the magnetic coils being designed as disk coils with helicoidally extending coil windings and annularly surrounding the pole shoe end of the assigned pole shoe to form a magnetic coil/pole shoe gap, wherein said magnetic coil arrangement comprises:

a first coil box surrounding a first pole shoe;

a first magnetic coil disposed in said first coil box annularly surrounding said first pole shoe;

a second coil box surrounding a second pole shoe;

a second magnetic coil disposed in said second coil box annularly surrounding said second pole shoe;

said first and second coil boxes including at least one cooling air admission port for connection to a cooling air pump and at least one cooling air discharge port for discharging cooling air circulated by said air pump.

2. The arrangement of claim 1, including a magnetic yoke composed of ferrite block segments, said ferrite block segments including ferrite plates aligned in rows in the direction of magnetic flow, insulation/cooling gaps separating said ferrite plates transverse to the direction of magnetic flow through which cooling air can be conveyed, and separators disposed between adjacent ferrite plates to create said insulation/cooling gaps and bonding said ferrite plates together to form said block segments into yoke elements.

3. The arrangement of claim 2 wherein said first and second pole shoes are round and composed of wedge-shaped ferrite block segments fitted together, separators being inserted between adjacent wedge-shaped ferrite block segments to provide insulation/cooling gaps there between and bonding said ferrite block segments together to form said pole shoes, and an axial tubular bore is created through said pole shoe to form a tubular pole shoe so that cooling air can be introduced through the tubular bore.

4. The arrangement of claim 1 including pole shoe plates spaced below and extending laterally beyond ends of said pole shoes, and an intended pole shoe area defined below said pole shoe ends which forms part of a coil box bottom wall, separators inserted between the pole shoe ends and the pole shoe plates in said indented area to provide insulation/cooling gaps there between.

5. The arrangement of claim 4, wherein said pole shoe plates are reduced in thickness in said indented area as compared to the thickness of the remainder of the coil box bottom wall, and an annular air outlet gap for said insulation/cooling gap defined between edges of said pole shoe ends cooling air outlet.

6. The arrangement of claim 1 when said pole shoes are circular in cross-section, and said pole shoes include circular pole shoe end surfaces on opposing sides of said exposure volume gap, said magnetic coil being made circular ring, said magnetic coil surrounding said pole shoe ends, and said coil boxes surrounding associated magnetic coils, and at least one cooling air admission port located in each said coil box side.

7. The arrangement of claim 1 including a support structure for said coil windings of said magnetic coil disposed within said coil box, said support structure including lower coil carriers provided on the bottom, and upper coil carriers provided above said lower coil carriers, said coil carriers being arranged radially extending and angularly spaced relative to each other.

8. The arrangement of claim 7 wherein said coil carriers are connected by insulating rods which are radially spaced and approximately axially aligned, and including insertion sections formed between said insulating rods in which the helicoidally extending coil windings are retained, said coil windings being raised in respect to the coil box bottom wall forming a radially exterior annular cooling air inlet gap for cooling air there between, and an air discharge gap defined between the top side coil carriers and above said coil windings for the discharge of air over the coil windings.

9. The arrangement as in claim 8, wherein the insulating rods are designed as round ceramic rods.

10. The coil arrangement in claims 8 wherein the coil carriers are wedge shaped so that the radially outermost coil windings are raised further from the coil box bottom wall than the coil windings which are radially further inside.

11. The coil arrangement of claim 10, including bottom-parallel air baffle plates extending with a lower air baffle plate being longer and wider than an upper air baffle plate in the annular cooling air inlet gap between the bottom coil carriers.

12. The coil arrangement of claim 11, wherein the air baffle plates are connected via spacers with the coil box bottom wall.

13. The coil arrangement in claims 8 wherein the coil carriers have location holes into which said insulating rods are inserted and in which they are held, said bottom coil carriers are fastened with the coil box bottom wall, said top coil carriers are detachably fastened to said coil box top wall and are detachably fastened by means of support columns attached to the coil box bottom wall, and an integral coil box structure connections between said coil box bottom wall, coil box side walls, and connection elements with an adjacent magnetic yoke element.

14. The coil arrangement of claim 7 wherein the coil box bottom wall, the coil box side walls, the coil box top wall, and a thin inside wind wall radially surrounding the magnetic coil which is separated from the coil box bottom wall by an annular cooling air inlet gap, form a circumferential wind box, and an annular air guide wall surrounding said magnetic coil on an inside thereof to create an annular gap to dissipate the pole shoe cooling air between said air guide wall and an adjacent pole shoe wall.

15. The coil arrangement of claim 1 wherein said magnetic yoke has a general M shape which includes a three-leg.

16. A magnetic field applicator having a magnetic coil arrangement for heating magnetic or magnetizable substances or solids in biological tissue comprising:

a magnetic yoke with a first pole and second pole a first magnetic coil annularly surrounding a first pole shoe;

a first coil box surrounding said first magnetic coil and said first pole shoe;

a second magnetic coil annularly surrounding said a second pole shoe;

a second coil box surrounding said second magnetic coil and said second pole shoe;

said first and second coil boxes including at least one cooling air admission port for connection to a cooling air pump and at least one cooling air discharge port for discharging cooling air circulated by said air pump.

17. The arrangement of claim 16 including an axial tubular bore created through said pole shoes to form tubular pole shoes so that cooling air can be introduced through the tubular bores of said pole shoes.

18. The arrangement of claim 16 including insulation/cooling gaps formed between ends of said pole shoes and pole shoe plates spaced below said pole shoe ends within said coil boxes.

19. The arrangement of claim 18 wherein each said coil box includes a bottom wall, and including an annular air outlet gap defined between said end of said bottom wall in the area of said pole shoe plate for discharge of cooling air from said insulation/cooling gap.

20. The arrangement of claim 16 including a support structure for said coil windings of said magnetic coil disposed within said coil box, said support structure supports said coil windings in a raised configuration in which the radially outermost coil windings are raised further from the coil box bottom wall than the coil windings with are radially further inside to define an air inlet gap between said coil windings and said bottom wall for the discharge of air over the coil windings.

21. The arrangement of claim 20 including a pole gap defined between each said magnetic coil winding and pole shoe within said coil box for the circulation of cooling air.

* * * * *